United States Patent [19]

Chomczynski

[11] Patent Number: 4,843,155
[45] Date of Patent: Jun. 27, 1989

[54] PRODUCT AND PROCESS FOR ISOLATING RNA

[76] Inventor: Piotr Chomczynski, 727 Martin Luther King Dr., Cincinnati, Ohio 45220

[21] Appl. No.: 123,107

[22] Filed: Nov. 19, 1987

[51] Int. Cl.$^4$ ............................................. C02H 21/02
[52] U.S. Cl. ........................................ 536/27; 536/28; 536/29
[58] Field of Search .................... 536/27, 28, 29, 24

[56] References Cited

U.S. PATENT DOCUMENTS 3,147,185  9/1964  Charney ............................. 536/24
3,389,133  6/1968  Gutcho ............................... 536/24

OTHER PUBLICATIONS

R. A. Cox, Methods in Enzymology, 12(B): 120–129, (1968).
J. M. Chirgwin, et al., Biochem 18: 5294–5299 (1979).
J. R. Feramisco, et al., Molecular Cloning, 194–195, Cold Spring Harbor Laboratory, Cold Spring Harbor, N.Y.
Kochetkov et al., Organic Chem. of Nucleic Acids, Part A 1971, Plenium Press, pp. 23–28.

Primary Examiner—Ronald W. Griffin
Assistant Examiner—L. Eric Crane
Attorney, Agent, or Firm—Wood, Herron & Evans

[57] ABSTRACT

The present invention discloses a novel method for isolating RNA from biological tissue samples and a novel solvent adapted for use in the disclosed method. The method employs a single extraction using the solvent containing guanidinium and phenol. The solvent is stable for about one month at room temperature without any appreciable phenol oxidation or decomposition. Application of the disclosed method and solvent to a biological tissue sample results in the isolation of a high yield of RNA in a substantially pure and undegraded form. The whole procedure can be completed in three hours, much more quickly than other procedures.

7 Claims, 1 Drawing Sheet

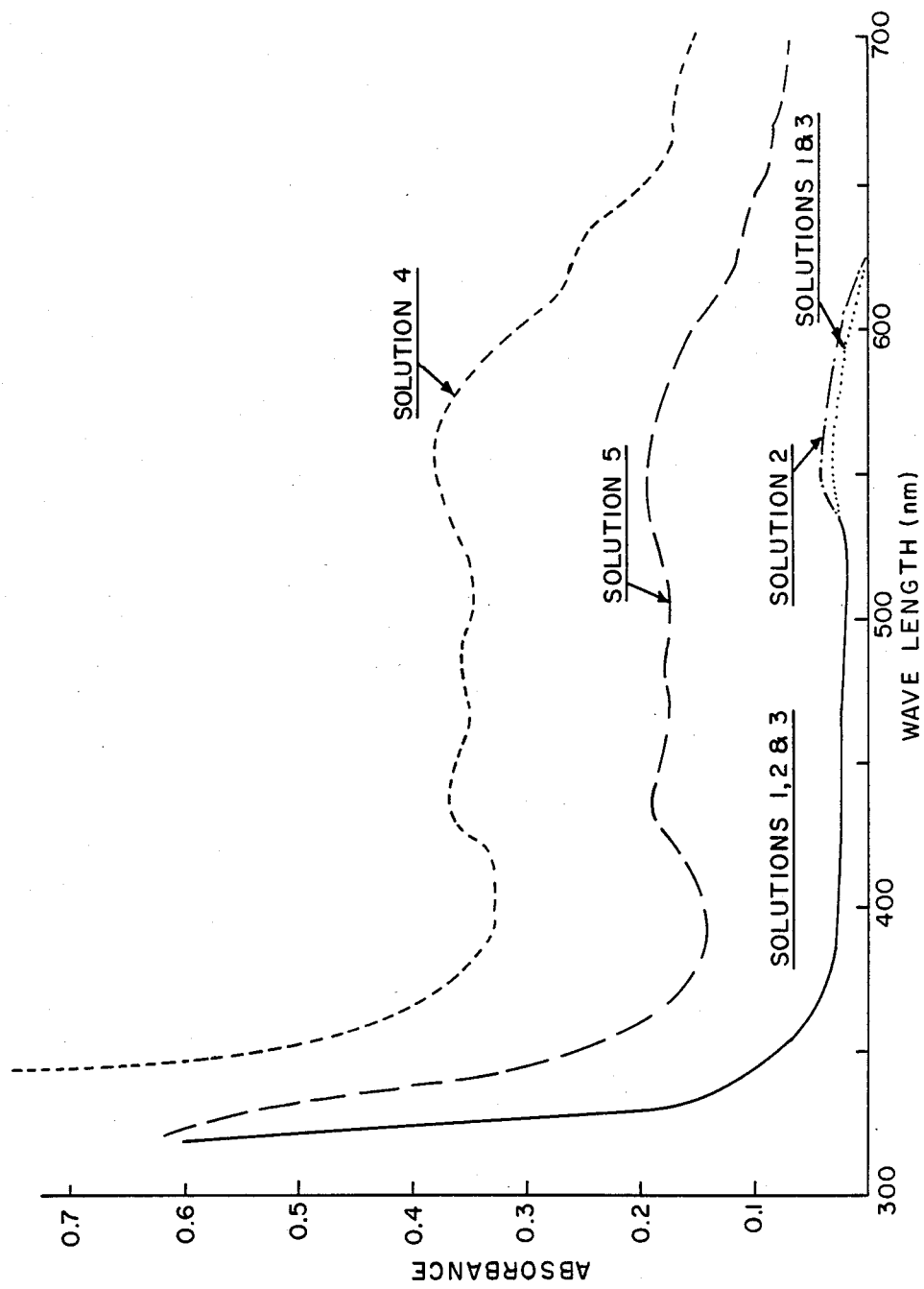

PRODUCT AND PROCESS FOR ISOLATING RNA

FIELD OF THE INVENTION

This invention relates to the isolation of ribonucleic acid from biological tissue.

BACKGROUND

The extensive research being conducted in the field of molecular biology has caused a rising demand for pure, undegraded ribonucleic acid ("RNA"). RNA is obtained by extracting it from biological tissue in which it is present together with deoxyribonucleic acid (DNA) and proteins. The RNA must be separated from the DNA and proteins before it can be used in experimental work such as gene expression studies. With the increased demand for RNA has come a need for a more efficient and productive method for isolating it from the biological tissues in which it is found.

THE PRIOR ART

Guanidinium thiocyanate and guanidinium chloride are well known as effective protein denaturants, and the chloride has been employed as a deproteinization agent for isolating RNA, see Cox, R. A.: *Methods in Enzymology*, 12(B): 120-129 (1968). In the Cox procedure a suspension of ribosomes in a buffer is added to 6M guanidinium chloride. The RNA is precipitated by adding alcohol to the solution and the precipitate is recovered by centrifugation. At this point, the precipitate is not free of RNase (a contaminating enzyme which causes RNA degradation) and is purified by dissolution in 4M guanidinium chloride and re-precipitation by adding ethanol. The precipitate is again separated by centrifugation. If further purification is necessary, the precipitate is redissolved in guanidinium chloride and re-precipitated with ethanol. This procedure takes approximately two days to complete.

The current method-of-choice for isolating RNA is disclosed in Chirgwin, J. M. et al: *Biochem*, 18:5294-5299 (1979). In that procedure, RNA-containing tissue is homogenized in a solution containing guanidinium thiocyanate, sodium citrate and 2-mercaptoethanol, with the solution pH adjusted to 7 by adding sodium hydroxide. The homogenate is then centrifuged and the supernatant decanted and mixed with acetic acid (to lower the pH to 5) and absolute ethanol. Overnight storage at $-20°$ C. precipitates the RNA and it is recovered in pellet form after centrifugation. The pellet is redissolved in a buffered guanidine hydrochloride solution and reprecipitated by adding acetic acid and ethanol. The last step is repeated and the isolated RNA is recovered in pellet form. Alternatively, the RNA can be separated from the guanidinium thiocyanate homogenate by ultracentrifugation through a dense cushion of cesium chloride. This method is disadvantageous in that it may take up to 2 days to obtain results and it may require the use of expensive ultracentrifugation equipment which reduces the total amount of RNA recoverable because of the limited number of samples that can be simultaneously processed.

In another RNA-isolating procedure, shown in Feramisco, J. R. et al: *Molecular Cloning*, 194-195, Cold Spring Harbor Laboratory, Cold Spring Harbor, N.Y. (1982), RNA-containing tissue is homogenized in a solution of 4M guanidinium isothiocyanate, 20% Sarkosyl (sodium lauryl sarkosinate) and 2-mercaptoethanol. An equal volume of heated phenol (60° C.) is added to the homogenate along with a sodium acetate solution of pH 5.2. Then an equal volume of chloroform is added and the mixture is cooled and centrifuged. The aqueous phase is recovered and reextracted with phenol and/or chloroform about seven more times before the final product is recovered. This procedure is slow and cumbersome in that multiple extractions are required and it takes approximately two days to recover the available RNA.

Because the known methodologies for isolating pure, undegraded RNA are time consuming, repetitive or require expensive ultracentrifugation equipment, there is a need for a better method for RNA isolation.

SUMMARY OF THE INVENTION

The present invention is predicated in part upon a faster and more efficient method for isolating RNA from a biological tissue sample in a substantially pure and undegraded form. This method is advantageous in that it isolates an unexpectedly high yield of RNA in a substantially pure and undegraded form, even in a single step extraction. The whole procedure can be completed in as little as three hours, much more quickly than the prolonged periods required for other RNA extraction procedures. An additional advantage of this method is that it does not require the use of an ultracentrifuge, and thus the volume limitation of that device is not present.

Another aspect of the invention is a novel solvent, comprising phenol and acid guanidinium or a salt thereof, for use in carrying out the RNA isolation method. This solvent is surprisingly effective in that combining acid guanidinium or a salt thereof with phenol greatly reduces the rat of oxidation and decomposition of phenol that normally accompanies exposure to air and light. The solvent can be stored conveniently at about 4° C. for at least about three months or at room temperature for at least about one month, whereas phenol usually must be kept at about $-20°$ C. and preferably under nitrogen gas or in the presence of 8-hydroxyquinoline in order to prevent the oxidation and decomposition which renders phenol unusable in RNA isolation techniques.

In the preferred practice of the method, the tissue sample is homogenized with a novel denaturing solvent which comprises 2 to 5M guanidinium in phenol. (As used hereinafter the term "guanidinium" refers to and includes both acid guanidinium and the salts thereof, including, but not limited to, guanidinium thiocyanate and guanidinium chloride). The 2-5M strength solution effects a significant dissociation of the nucleoprotein into its nucleic acid and protein moieties, which is an essential step in the isolation of RNA. The solvent preferably also contains an additional antioxidant such as 2-mercaptoethanol and a sufficient amount of buffer to maintain the pH of the solvent at approximately 4. The buffer may be, but is not limited to, sodium acetate or sodium citrate.

The preferred method of this invention includes the further step of separating the homogenate, as prepared above, into two phases by the addition of a water-insoluble organic solvent such as chloroform or carbon tetrachloride. It has been determined that this phase separation is very advantageously conducted with the solvent at a pH of approximately 4 and at an organic solvent concentration of approximately 10%. Extraction at pH and organic solvent concentrations above or below these levels results in a significantly lower degree of RNA isolation and thus requires repeated extractions and more time to achieve the desired RNA isolation. Once the organic solvent has been added, the solution is agitated, cooled and centrifuged to promote phase separation. The result is a two-phase mixture comprising an upper aqueous phase and a lower organic phase wherein the RNA is concentrated exclusively in the aqueous phase and the DNA and proteins are in the organic phase and the interphase.

The preferred method of this invention includes the further step of separating the aqueous phase formed in the preceding step from the organic phase and adding to the aqueous phase a lower alcohol, preferably isopropanol, in an approximate 1:1 volume ratio. The RNA is insoluble in the 50% alcohol mixture and is thus precipitated. The solution is then cooled and centrifuged and the RNA is recovered in pellet form by removing the supernatant.

The preferred method of this invention includes the final step of washing the RNA pellet with ethanol by vortexing and subsequent centrifugation, thus recovering a high yield of RNA in a substantially pure and undegraded form.

DETAILED DESCRIPTION

The preferred practice of this invention is shown by the following examples.

PREPARATION OF THE SOLVENT

EXAMPLE 1

The most preferred embodiment of the solvent of this invention is made by combining 468 ml of a 4M solution of guanidinium thiocyanate (Fluka), 25 ml of sodium acetate, 1.8 ml of 2-mercaptoethanol and 495 ml of phenol (Fisher). Mixing is carried out at room temperature. Optimally the mixture is approximately 50% phenol by volume, but the advantages of this invention are also obtained when the resulting mixture contains from about 40% to about 60% phenol by volume. As the percentage of phenol is changed, the amount of buffer and guanidinium must be adjusted so that the pH of the mixture is about 4.

EXAMPLE 2

The novel solvent of this invention is also producible by using guanidinium chloride, rather than guanidinium thiocyanate in the composition described in Example 1. The most effective range of proportions is similar to that given in Example 1.

EXAMPLE 3

The novel solvent of this invention is also producible by using sodium citrate rather than sodium acetate in the composition described in Example 1. The most effective range of proportions is similar to that given in Example 1.

EXAMPLE 4

The novel solvent of this invention is also producible by leaving 2-mercaptoethanol out of the composition described in Example 1. The most effective range of proportions of the other components is similar to that given in Example 1.

Stability of the Solvent

It is well known that phenol tends to degrade rapidly during storage at room temperature; typically a given small quantity becomes unsuitable for use within about one month, unless it is stored at about $-20°$ C.

The guanidinium-phenol solvent of this invention has a significantly longer shelf-life than that of phenol alone under similar conditions. It is theorized that this is because the guanidinium inhibits the oxidation and decomposition of phenol that ordinarily results from exposure to light and air.

Phenol stabilization is shown by a comparison of the optical density (OD) profiles obtained by scanning various samples using a Gilford spectrophotometer. The OD profiles for five samples are shown in the drawing wherein the horizontal axis represents wavelength over the range 300–700 nm and the vertical axis represents absorbance. The OD profiles indicate the presence or absence of phenolic oxidation end products which cause breakdown and crosslinking of nucleic acids and thus render phenol unusable in RNA isolation techniques. The samples are prepared using the following reagents: phenol, crystal ACS grade (Fisher); guanidinium thiocyanate, purum p.a. (Fluka); and distilled water.

The numbered OD profiles shown in the drawing correspond to the following five samples. Solution 1: 50 ml of water-saturated phenol is mixed with 50 ml of 4M guanidinium thiocyanate. Immediate OD scan shows a negligible presence of phenolic oxidation end products. Solution 2: prepared in the same manner as Solution 1 and stored for one month at room temperature exposed to light ten hours daily. OD scan after storage shown an OD profile nearly identical to that of the freshly prepared phenol-guanidinium Solution 1. Solution 3: 50 ml of freshly prepared, water-saturated phenol. Immediate OD scan shows a negligible presence of phenolic oxidation end products. Solution 4: prepared in the same manner as Solution 3 and stored for one month at room temperature exposed to light ten hours daily. OD scan after storage shows an OD profile indicating an unacceptably high level of phenolic oxidation end products. Solution 5: prepared and stored in the same manner as Solution 4 and mixed with a equal volume of 4M guanidinium thiocyanate immediately prior to OD scanning. The OD profile indicates that addition of guanidinium thiocyanate to phenol after the phenol has been stored at room temperature for one month does not affect the light absorption of the phenol oxidation products. The lower OD of Solution 5 is caused by dilution of phenol with guanidinium thiocyanate.

The comparison made in the drawing shows that guanidinium effectively diminishes the oxidation and decomposition rates of phenol when the two are mixed and stored at room temperature. Thus the guanidinium-phenol solution remains stable an usable for at least about one month at room temperature. Similar tests show that the guanidinium-phenol solution remains stable and usable for at least about three months when stored at $4°$ C.

Practice of the Method

EXAMPLE 5

The method of isolating RNA from a biological tissue sample employs a solvent which is prepared as shown in Example 1 (the "Solvent").

25 milligrams of mouse anterior pituitaries are homogenized in 0.8 ml of Solvent with a few strokes in a glass-Teflon homogenizer to form a homogenate. 0.08 ml of chloroform (ACS grade) is added to the homogenate and the samples are vigorously shaken for 15 seconds and then cooled on ice for 15 minutes. The suspension is then centrifuged for 15 minutes in an Eppendorf centrifuge at 12,000 g and 4° C. At this point, the homogenate forms two phases: the lower phenol-chloroform phase (containing DNA and proteins) and the upper aqueous phase (containing RNA).

The aqueous phase (approximately 0.4 ml) is transferred to a fresh tube by means of a pipette. Isopropanol (ACS grade) is added in equal volume (0.4 ml) to the separated aqueous phase and the resulting solution is stored for 45 minutes at −20° C. in a laboratory freezer. The solution is then centrifuged for 15 minutes in the Eppendorf centrifuge at 12,000 g and 4° C. and the RNA precipitate forms a white pellet at the bottom of the tube. The supernatant is removed and the RNA pellet is washed twice with 0.8 ml of 75% ethanol (ACS grade) by vortexing and subsequent centrifugation for 8 minutes at 12,000 g and 4° C.

The pellet is dried briefly under vacuum for 10-15 minutes. The RNA pellet is then dissolved by vortexing in 0.05 ml of 0.5% SDS (sodium dodecyl sulfate) or in 0.05 ml of 1 mM EDTA (ethylene diamine tetraacetic acid), pH 7.

The amount of protein contamination in the isolated RNA is determined spectrophotometrically using a Gilford spectrophotometer. The procedure involves placing .3-4 μl of the RNA-SDS solution into a quarz cuvette and adding distilled water until the 1 ml cuvette is full. The cuvette is then placed in the spectrophotometer and light absorption is measured at 260 and 280 nm. Proteins exhibit maximum absorbance at 280 nm and the ratio of absorbances ($A_{260}/A_{280}$) for pure RNA is approximately 2. Experimental results using the method and solvent of this invention show a 260/280 ratio of 1.9-2.0 as compared to a 260/280 ratio of 1.79 obtained using the Chirgwin method.

An additional test of the purity of the isolated RNA is to determine the level of DNA contamination. Two alternative procedures may be employed to make this determination: Burton's reaction, Burton, K.: *Biochem. J.*, 62: 315-322 (1956); or radioactively-labelled plasmid DNA, using pBR 322 labelled by nick-translation with $P^{32}$. Both methods indicated an absence of DNA in the RNA isolated using the method and solvent of this invention.

Finally, the quality of the growth hormone messenger RNA (GH mRNA) is determined by Northern dot blot hybridization. This procedure shows the absence of degraded forms of mRNA in the RNA isolated using the method and solvent of this invention.

What is claimed is:

1. A method of isolating RNA from a biological tissue sample including RNA, DNA and proteins, comprising:
   homogenizing said tissue sample with a denaturing solvent which consists essentially of a guanidinium compound selected from the group consisting of guanidinium thiocyanate and guanidinium chloride, phenol and a buffer in an amount sufficient to maintain said solvent at or about pH 4, to form a homogenate;
   adding a water-insoluble organic solvent to said homogenate and centrifuging to form a two-phase mixture having an aqueous phase and an organic phase, wherein said RNA is concentrated in said aqueous phase, and said DNA and proteins are concentrated in said organic phase or in the interphase;
   precipitating said RNA from said aqueous phase by adding a lower alcohol to said aqueous phase; and recovering the precipitated RNA by centrifugation of said aqueous phase and decanting the supernatant liquid.

2. A method of claim 1 wherein said denaturing solvent is stored for more than about four weeks at substantially room temperature before use in said method.

3. The method of claim 1 wherein said tissue sample is homogenized in said solvent in the proportion of about 2ml solvent/100 mg. tissue sample.

4. The method of claim 1 wherein said water-insoluble organic solvent is added to said homogenate in an amount equal to approximately 1/10 the volume of the homogenate.

5. The method of claim 1 wherein said lower alcohol is added in approximately equal volume to said aqueous phase.

6. The method of claim 1 including the further step of washing the precipitated RNA in ethanol and drying it.

7. A solvent, which remains stable after prolonged storage, for extracting RNA from biological tissue when said solvent is added to the tissue, said solvent consisting essentially of:
   a solution of a guanidinium compound selected from the group consisting of guanidinium thiocyanate and guanidinium chloride, phenol and a buffer in an amount sufficient to maintain said solvent at or about PH 4, said solution present in a proportion which is effective both to substantially reduce oxidation and decomposition of said phenol and thereby to maintain said solvent stable during storage in comparison to phenol stored alone, and, in conjunction with said phenol, to separate RNA from said biological tissue, said proportion of said solution making up from about 40% to about 60% of said solvent by volume.

* * * * *